United States Patent
Steinmetzer et al.

(10) Patent No.: US 11,073,518 B2
(45) Date of Patent: Jul. 27, 2021

(54) PREFABRICATED MICROPARTICLE FOR PERFORMING A DETECTION OF AN ANALYTE

(71) Applicant: BLINK AG, Jena (DE)

(72) Inventors: Katrin Steinmetzer, Jena (DE); Stephan Hubold, Jena (DE); Thomas Ellinger, Jena (DE); Eugen Ermantraut, Jena (DE); Torsten Schulz, Jena (DE)

(73) Assignee: BLINK AG, Jena (DE)

( * ) Notice: Subject to any disclaimer, the term of this patent is extended or adjusted under 35 U.S.C. 154(b) by 0 days.

(21) Appl. No.: 16/475,109

(22) PCT Filed: Dec. 22, 2017

(86) PCT No.: PCT/EP2017/084370
§ 371 (c)(1),
(2) Date: Jun. 30, 2019

(87) PCT Pub. No.: WO2018/122162
PCT Pub. Date: Jul. 5, 2018

(65) Prior Publication Data
US 2019/0331677 A1    Oct. 31, 2019

(30) Foreign Application Priority Data
Dec. 30, 2016 (EP) .................................. 16207455

(51) Int. Cl.
*G01N 33/543* (2006.01)
*C12Q 1/6848* (2018.01)

(52) U.S. Cl.
CPC ..... *G01N 33/54393* (2013.01); *C12Q 1/6848* (2013.01); *G01N 33/54313* (2013.01)

(58) Field of Classification Search
CPC ......................... G01N 33/54393; C12Q 1/6848
See application file for complete search history.

(56) References Cited

U.S. PATENT DOCUMENTS

| | | | |
|---|---|---|---|
| 2010/0267109 A1* | 10/2010 | Rothberg | C08F 222/38 435/183 |
| 2015/0293102 A1 | 10/2015 | Shim | |

FOREIGN PATENT DOCUMENTS

| | | |
|---|---|---|
| WO | 2011/100057 A2 | 8/2011 |
| WO | 2015/048173 A2 | 4/2015 |

OTHER PUBLICATIONS

Shuga et al, Single molecule quantitation and sequencing of rare translocations using microfluidic nested digital PCR, 2013, Nucleic Acids Research, 41, e159, pp. 1-11 (Year: 2013).*
Shuga et al, Single molecule quantitation and sequencing of rare translocations using microfluidic nested digital PCR, 2013, Nucleic Acids Research, 41, e159, pp. 1-11 supplementary information, pp. 1-18 (Year: 2013).*
Cube Biotech agarose matrices brochure, printed by the examiner on on Jul. 23, 2020, pp. 1-8 (Year: 2020).*
Thermoscientific brochure NHS activated agarose dry printed by the examiner on on Jul. 25, 2020, pp. 1-8 (Year: 2020).*
Haushalter et al, Multiplex Flow Assays, 2016, ACS Omega, 1, 586-599 (Year: 2016).*
Dressman, Devin et al., "Transforming single DNA molecules into fluorescent magnetic particles for detection and enumeration of genetic variations." PNAS, vol. 100(15): 8817-8822, Jul. 22, 2003.
Kan, Cheuk W. et al., "Isolation and detection of single molecules on paramagnetic beads using sequential fluid flows in microfabricated polymer array assemblies." Lab Chip 12(5):977-985, Jan. 1, 2012.
Kim, Soo Hyeon et al., "Large-scale femtoliter droplet array for digital counting of single biomolecules." Lab Chip vol. 12(23):4986-4991, Jan. 1, 2012.
Kumaresan, Palani et al., "High-Throughput Single Copy DNA Amplification and Cell Analysis in Engineered Nanoliter Droplets." Anal. Chem. vol. 80(10):3522-3529, May 1, 2008.
Zeng, Yong et al., "High-Performance Single Cell Genetic Analysis Using Microfluidic Emulsion Generator Arrays." Anal. Chem. 82(8):3183-3190, Apr. 15, 2010.

* cited by examiner

*Primary Examiner* — Narayan K Bhat
(74) *Attorney, Agent, or Firm* — Saliwanchik, Lloyd & Eisenschenk

(57) ABSTRACT

The present invention relates to a prefabricated microparticle for performing detection, preferably a digital detection and/or quantitation of an analyte. Furthermore, it also relates to a detection and/or quantitation of multiple analytes by prefabricated microparticles. It also relates to a collection of such prefabricated microparticles and to the use of such microparticle(s) and/or of such collection. Furthermore, the present invention also relates to a method of performing a detection and/or quantitation of an analyte in a sample wherein a microparticle or collection of microparticles are used. In one embodiment, in the collection of microparticles, individual microparticles are tailored for the detection of specific analytes and can be distinguished from each other by a specific label indicating the respective analyte for which the individual microparticle is specific.

22 Claims, 6 Drawing Sheets
Specification includes a Sequence Listing.

A
5x magnification, transmission image, DABs in oil

B
5x magnification, transmission image, DABs in PBS

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: sense primer
```

-continued

```
<400> SEQUENCE: 1
gcagtggcgc ccgaacagg                                                  19

<210> SEQ ID NO 2
<211> LENGTH: 22
<212> TYPE: DNA
<213> ORGANISM: Artificial Sequence
<220> FEATURE:
<223> OTHER INFORMATION: antisense primer 1

<400> SEQUENCE: 2
actgacgctc tcgcacccat ct                                              22

<210> SEQ ID NO 3
<211> LENGTH: 23
<212> TYPE: DNA
<213> ORGANISM: Artificial Sequence
<220> FEATURE:
<223> OTHER INFORMATION: antisense primer 2

<400> SEQUENCE: 3
tgacgctctc gcacccatct ctc                                             23

<210> SEQ ID NO 4
<211> LENGTH: 125
<212> TYPE: DNA
<213> ORGANISM: Artificial Sequence
<220> FEATURE:
<223> OTHER INFORMATION: oligonucleotide for labelling detection
      antibody

<400> SEQUENCE: 4
gcgtcagacc ccgtagaaaa gatcaaagga tcttcttgag atcctttttt tctgcgcgta     60
atctgctgct tgcaaacaaa aaaccaccg ctaccagcgg tggtttgttt gccggatcaa    120
gagct                                                               125

<210> SEQ ID NO 5
<211> LENGTH: 20
<212> TYPE: DNA
<213> ORGANISM: Artificial Sequence
<220> FEATURE:
<223> OTHER INFORMATION: forward primer for PCR in embodiment 3

<400> SEQUENCE: 5
agctcttgat ccggcaaaca                                                 20

<210> SEQ ID NO 6
<211> LENGTH: 20
<212> TYPE: DNA
<213> ORGANISM: Artificial Sequence
<220> FEATURE:
<223> OTHER INFORMATION: reverse primer for PCR in embodiment 3

<400> SEQUENCE: 6
gcgtcagacc ccgtagaaaa                                                 20
```

PREFABRICATED MICROPARTICLE FOR PERFORMING A DETECTION OF AN ANALYTE

CROSS REFERENCE TO RELATED APPLICATIONS

This application is a National Stage Application of International Application Number PCT/EP2017/084370, filed Dec. 22, 2017; which claims priority to European Patent Application No. 16207455.3, filed Dec. 30, 2016.

The Sequence Listing for this application is labeled "SeqList-26Jun19-ST25.txt", which was created on Jun. 26, 2019 and is 2 KB. The entire content is incorporated herein by reference in its entirety.

The present invention relates to a prefabricated microparticle for performing a detection and/or quantitation of an analyte. Furthermore it also relates to a detection and/or quantitation of multiple analytes by prefabricated microparticles. It also relates to a collection of such prefabricated microparticles and to the use of such microparticle(s) and/or of such collection. Preferably the detection is a digital detection. Furthermore, the present invention also relates to a method of performing a detection and/or quantitation of an analyte or of multiple analytes in a sample wherein a microparticle or a collection of microparticles are used. In one embodiment, in the collection of microparticles, individual microparticles are tailored for the detection of specific analytes and can be distinguished from each other by a specific label indicating the respective analyte for which the individual microparticle is specific.

Numerous techniques and methods have been devised for the detection of analytes in a sample. The sensitive and quantitative detection of an analyte is, in an ideal world, digital. To this end, the sample is distributed to a number of reaction spaces, and in each reaction space, there is one analyte molecule at a maximum. In this manner, despite the overall low amount of analyte, a high analyte concentration is reached with reference to the background, and thus the efficiency of the reaction is increased. The generated signal is concentrated to a small confined space and can thus be easily detected. As early as 1961, the activity of individual enzyme molecules was measured in aqueous droplets in oil (Rotman, 1961, PNAS, 47: pp. 1891-1991). This proved the feasibility of the detection of activity of a single enzyme molecule and thus the possibility of performing digital assays. With the development and increased distribution of molecular amplification processes, the concept of a "limiting dilution" found its way into the analytics of nucleic acids (Sykes et al., 1992, Biotechniques, 13: pp. 444-449). A compartmentalization was originally reached by dividing the analyte/target molecule containing sample solution onto individual reaction spaces of a microtiter plate. Subsequently, a considerably higher number of reaction spaces was achieved by using capillaries and microstructured substrates (Kalinina et al. 1997, Nucleic Acids Research, 25: pp. 1999-2004). Likewise primer oligonucleotides which were immobilized to microparticles were used in combination with water/oil immersions (Vogelstein et al. 1999, PNAS, 96: pp. 9236-9241). There are also formats available for performing digital immunoassays in which microstructured substrates are used which allow the generation of small amounts of aqueous solution and which thus produce a plurality of reaction spaces (Rissin et al. 2006, Nanolett. 6: pp. 520-523). In essence, the methodology that is nowadays available for performing detection of an analyte typically involve complex devices for the generation of micro reaction spaces or for performing the respective detection tests. Accordingly, it was an object of the present invention to provide for a methodology for performing a detection, preferably a digital detection of an analyte in a sample which methodology is easy to handle and which can be performed without extensive efforts on the part of the apparatuses used. It is also an object of the present invention to provide for a methodology that is versatile and that can be tailored towards different analytes, yet is universally employable and can be easily adapted to different analytes. It is furthermore an object to provide for a detection method that allows for the enrichment of analytes from different volumes of liquid without having to adjust the final volume of the detection reaction.

In one aspect, the present invention relates to a method of performing a detection, preferably a digital detection, of an analyte in a sample, said method comprising the steps:

a) providing a prefabricated microparticle which has a surface and includes a void volume for receiving an aqueous solution, wherein said particle is dispersible in a non-aqueous medium and, upon dispersion in a non-aqueous medium, provides for a defined reaction space in such non-aqueous medium, in which defined reaction space a chemical or biochemical reaction indicating the presence of an analyte can be performed, and wherein said prefabricated microparticle comprises a capture agent that, upon exposure of said microparticle to a sample surrounding said prefabricated microparticle and containing an analyte, selectively and specifically binds the analyte to be detected and that, upon binding of the analyte to the capture agent, forms a complex between said capture agent and said analyte, wherein said capture agent binds the analyte from a sample surrounding said prefabricated microparticle, and wherein said prefabricated microparticle further comprises a detection agent that is specific for the analyte or said complex between said capture agent and said analyte, and that binds said analyte or said complex between said capture agent and said analyte;

b) exposing said prefabricated microparticle to an aqueous sample suspected of containing an analyte to be detected, thus allowing the capture agent to selectively and specifically bind the analyte to be detected, if present;

c) placing the prefabricated microparticle into a non-aqueous phase, e.g. an oil phase and using the void volume of said prefabricated microparticle as a defined reaction space in which a chemical or biochemical reaction indicating the presence of an analyte, is performed, by either d1) detecting the detection agent bound to said analyte or to said complex between said capture agent and said analyte; or d2) amplifying the analyte, if present, by way of an amplification reaction, and detecting the thus amplified product by means of said detection agent, wherein said analyte is a nucleic acid and said amplification reaction is a nucleic acid amplification such as, for example, PCR, TMA, NASBA, LAMP, 3SR, SDA, RCA, LCR, RPA, NEAR, or d3) performing a signal amplification reaction, e.g. a nucleic acid amplification if a nucleic acid is or forms part of said detection agent, or e.g. an enzyme-based amplification of a signal, e.g. in the form of a label, such as a dye or fluorophor, if an enzyme is or forms part of said detection agent, and detecting the thus amplified signal.

In one embodiment, said prefabricated microparticle is provided as a prefabricated microparticle which is dried, preferably freeze-dried.

In one embodiment, said prefabricated microparticle is not an in-situ generated microparticle, preferably not a microparticle that is in-situ generated at the site or in the reaction, at or during which analyte detection is to take place.

In one embodiment, the prefabricated microparticle is a porous microparticle.

In one embodiment, said prefabricated microparticle has an interstitial pore space that allows the microparticle to receive or take up a liquid such as an aqueous sample, and, if present, any solute therein, such as an analyte.

In one embodiment, the capture agent is predominantly located on the surface of said prefabricated microparticle, such that the prefabricated microparticle is capable of enriching and concentrating an analyte located outside of the microparticle.

In one embodiment, said prefabricated microparticle is reconstituted in an aqueous solution, preferably either during step a) or step b), and, upon reconstitution, receives such aqueous solution in its void volume.

In one embodiment, said detection agent is included in said prefabricated microparticle during a prefabrication process or is included in said aqueous solution the present invention and thus becomes part of the prefabricated microparticle upon reconstitution.

In one embodiment, said prefabricated microparticle is made of a gel-forming agent, such gel-forming agent being preferably liquefiable upon the application of heat or light, or upon a change of pH, redox potential, ionic strength, temperature, magnetic field or electromagnetic radiation, or upon exposure to an enzyme or, if the gel-forming agent itself comprises an enzyme, to a substrate of such enzyme, or any combination of the foregoing.

In one embodiment, said gel-forming agent forms a matrix defining the surface and the void volume of said microparticle. In one embodiment, said matrix is a porous matrix.

In one embodiment, said gel-forming agent is selected from the group comprising
a) synthetic polymers prepared from their corresponding monomers, such as methylacrylate and acrylate, acrylamide and methacrylamide, cyclic lactams, styrene-based monomers;
b) silicone-based polymers, e.g. polydimethylsiloxanes and their copolymers;
c) naturally occurring polymers selected from polysaccharides, e.g. agarose, chitin, chitosan, alginate, carrageenan, cellulose, fucoidan, laminaran, gums selected from xanthan gum, arabic gum, ghatti gum, guar gum, locust bean gum, tragacanth gum, karaya gum and inulin; polypeptides, e.g. albumins, collagens, gelatins; polynucleotides; and combinations thereof.

In one embodiment, said capture agent is selected from antibodies or antibody fragments, nucleic acids, including aptamers, Spiegelmers, non-antibody proteins capable of specifically binding an analyte or analyte complex, such as receptors, receptor fragments, affinity proteins, e.g. streptavidin.

In one embodiment, said detection agent is selected from antibodies or antibody fragments, nucleic acids, including aptamers, Spiegelmers, non-antibody proteins, such as receptors, receptor fragments, affinity proteins, e.g. streptavidin, each of them optionally being labelled with a suitable reporter molecule, such as a dye, enzyme, chemical catalyst, or a mixture of reagents capable of starting a chemical reaction that produces an optically or otherwise detectable signal indicating the presence of the analyte to be detected.

In one embodiment, said prefabricated microparticle is specifically labelled.

In one embodiment, the method according to the present invention is performed using a collection of prefabricated microparticles, said prefabricated microparticles being as defined in any of the embodiments of the present invention.

In one embodiment, in said collection of prefabricated microparticles, said prefabricated microparticles are different from each other in that they are specific for different analytes to be detected, wherein each prefabricated microparticle is specifically labelled such that different prefabricated microparticles and their corresponding detected analytes can be distinguished by the specific labels of the prefabricated microparticles.

In one embodiment, said method involves the use of a prefabricated microparticle or of a collection of prefabricated microparticles as defined in the present invention, for performing a digital detection of an analyte or a plurality of analytes in a sample or for enriching and concentrating a plurality of analytes in a plurality of defined volumes, wherein, preferably, all of said defined volumes in said plurality of defined volumes are equal.

In one embodiment, after the step of exposing b), there is one or several washing steps.

In one embodiment, in step a), said prefabricated microparticles are provided in dried faun, and, in step b), said prefabricated microparticles are reconstituted in aqueous solution and then exposed to a sample suspected of containing an analyte to be detected, wherein, optionally after the step of reconstituting, there is one or several washing steps.

In one embodiment, in step b) the number of prefabricated microparticles and the number of analyte molecules in the sample are maintained or adjusted, as necessary, such that the binding of a single analyte molecule per prefabricated microparticle follows a Poisson distribution, preferably such that, on average, there is no more than one analyte molecule bound per microparticle, thus allowing the detection of a single analyte molecule per prefabricated microparticle.

In one embodiment, during step c), the prefabricated microparticle or the collection of prefabricated microparticles is suspended in the non-aqueous phase and/or is located on a solid substrate isolating each prefabricated microparticle from other prefabricated microparticles, if present, wherein, preferably, said solid substrate is a filter, a sieve, a substrate having a pattern of wells, recesses, grooves, channels, trenches, craters, holes, pillars or any combination of the foregoing.

In one embodiment, during or after step c), the gel-forming agent is liquefied, preferably through the application of heat or light, or by a change of pH, redox potential, ionic strength, temperature, magnetic field or electromagnetic radiation, or upon exposure to an enzyme or, if the gel-forming agent itself comprises an enzyme, to a substrate of such enzyme, or any combination of the foregoing, resulting in an aqueous droplet in a non-aqueous phase.

In one embodiment, said reaction space in which said chemical or biochemical reaction indicating the presence of an analyte, is performed, is defined by said void volume of said prefabricated microparticle and is not substantially larger than said void volume of said prefabricated microparticle.

In a further aspect, the present invention also relates to a method of performing a detection, preferably a digital detection, of an analyte in a sample, said method comprising the steps:

a) providing a prefabricated microparticle, which has a surface and includes a void volume for receiving an aqueous solution, wherein said particle is dispersible in an non-aqueous medium, and, upon dispersion in a non-aqueous medium, provides for a defined reaction space in such non-aqueous medium, in which defined reaction space a chemical or biochemical reaction indicating the presence of an analyte, can be performed, and wherein said prefabricated microparticle preferably is a porous microparticle that, upon exposure of said microparticle to a sample surrounding said prefabricated microparticle and containing an analyte, binds and/or immobilizes and/or receives the analyte from a sample surrounding said prefabricated microparticle, in the pores of said microparticle, by taking up a fraction of said sample in said pores, and wherein said prefabricated microparticle further comprises a detection agent that is specific for the analyte, and that binds said analyte;
b) exposing said prefabricated microparticle to an aqueous sample, suspected of containing an analyte to be detected, thus allowing the prefabricated microparticle to bind and/or immobilize and/or receive the analyte to be detected, if present;
c) placing the prefabricated microparticle into a non-aqueous phase, e.g. an oil phase and using the void volume of said prefabricated microparticle as a defined reaction space in which a chemical or biochemical reaction indicating the presence of an analyte, is performed, by either
d1) detecting the detection agent bound to said analyte; or
d2) amplifying the analyte, if present, by way of an amplification reaction, and detecting the thus amplified product by means of said detection agent, wherein said analyte is a nucleic acid and said amplification reaction is a nucleic acid amplification such as, for example, PCR, TMA, NASBA, LAMP, 3SR, SDA, RCA, LCR, RPA, NEAR, or
d3) performing a signal amplification reaction, e.g. a nucleic acid amplification, if a nucleic acid is or forms part of said detection agent, or, e.g. an enzyme-based amplification of a signal, e.g. in the form of a label, such a dye or a fluorophor, if an enzyme is or forms part of said detection agent, and detecting the thus amplified signal.

It should be noted that, in this aspect according to the present invention, the presence of a capture agent on the prefabricated microparticle is not necessary, as long as the prefabricated microparticle is capable of taking up liquid from the surroundings to which it is exposed. For example, such microparticle may be a porous microparticle, thus allowing the uptake of liquid and of an analyte present in said liquid in the porous microparticle, i.e. in the space provided for by the pores of said microparticle. Thus, according to this aspect of the present invention, the method even works if the prefabricated microparticle does not have a capture agent. Instead, any analyte present in a sample is received and taken up by a prefabricated microparticle according to the present invention simply due to its capability of receiving and taking up liquid therein. The presence of a capture agent increases the specificity and/or selectivity of the prefabricated microparticles for said analyte but is, however, not absolutely required or essential for the prefabricated microparticles according to the present invention to function. The presence of capture agents on the prefabricated microparticle may, however, in some embodiments increase the microparticle's capabilities of enriching and/or concentrating an analyte from a sample.

In a further aspect, the present invention relates to a prefabricated microparticle for performing a detection, preferably digital detection of an analyte in a sample, wherein said microparticle has a surface and includes a void volume for receiving an aqueous solution, wherein said particle is dispersible in a non-aqueous medium and, upon dispersion in a non-aqueous medium, is suitable to provide for a defined reaction space in such non-aqueous medium, in which defined reaction space a chemical or biochemical reaction indicating the presence of an analyte can be performed.

In one embodiment, the prefabricated microparticle according to the present invention is storable, preferably for a period of at least 2 months, more preferably at least 6 months.

In one embodiment, the prefabricated microparticle according to the present invention is dried, preferably freeze-dried.

In one embodiment, the prefabricated microparticle according to the present is not an in-situ generated particle, preferably not a particle that is in-situ generated at the site or in the reaction, at or during which analyte detection is to take place.

In one embodiment, said prefabricated microparticle is a porous microparticle.

Preferably, said prefabricated microparticle has an interstitial pore space that allows the microparticle to receive or take up a liquid, such as an aqueous sample, and, if present, any solute therein, such as an analyte.

In one embodiment said prefabricated microparticle comprises a capture agent that, upon exposure of said microparticle to a sample surrounding said microparticle and containing an analyte, selectively and specifically binds the analyte to be detected and that, upon binding of the analyte to the capture agent, forms a complex between said capture agent and said analyte, wherein said capture agent binds the analyte from a sample surrounding said microparticle.

In one embodiment, said capture agent is predominantly located on the surface of said microparticle, such that the microparticle is capable of enriching and concentrating an analyte located outside of the microparticle.

In one embodiment, the prefabricated microparticle according to the present invention further comprises a detection agent that is specific for the analyte or said complex between said capture agent and said analyte, and that binds said analyte or said complex between said capture agent and said analyte.

In one embodiment, said prefabricated microparticle is reconstituted in an aqueous solution and, upon reconstitution, receives such aqueous solution in its void volume.

In one embodiment, said detection agent is included in said prefabricated microparticle during a prefabrication process or is included in said aqueous solution in which it is reconstituted and thus becomes part of the microparticle upon reconstitution.

In one embodiment, said microparticle is made of a gel-forming agent, such gel-forming agent being preferably liquefiable upon the application of heat or light, or upon a change of pH, redox potential, ionic strength, temperature, magnetic field or electromagnetic radiation, or upon exposure to an enzyme or, if the gel-forming agent itself comprises an enzyme, to a substrate of such enzyme, or any combination of the foregoing.

In one embodiment, said gel-forming agent forms a matrix defining the surface and the void volume of said microparticle. In one embodiment, said matrix is a porous matrix.

In one embodiment, said gel-forming agent is selected from the group comprising a) synthetic polymers prepared from their corresponding monomers, such as methylacrylate and acrylate, acrylamide and methacrylamide, cyclic lactams, styrene-based monomers;
b) silicone-based polymers, e.g. polydimethylsiloxanes and their copolymers;
c) naturally occurring polymers selected from polysaccharides, e.g. agarose, chitin, chitosan, alginate, carrageenan, cellulose, fucoidan, laminaran, gums selected from xanthan gum, arabic gum, ghatti gum, guar gum, locust bean gum, tragacanth gum, karaya gum and inulin; polypeptides, e.g. albumins, collagens, gelatins; polynucleotides; and combinations thereof.

In one embodiment, said capture agent is selected from antibodies or antibody fragments, nucleic acids, including aptamers, Spiegelmers, non-antibody proteins capable of specifically binding an analyte or analyte complex, such as receptors, receptor fragments, affinity proteins, e.g. streptavidin.

In one embodiment, said detection agent is selected from antibodies or antibody fragments, nucleic acids, including aptamers, Spiegelmers, non-antibody proteins, such as receptors, receptor fragments, affinity proteins, e.g. streptavidin, each of them optionally being labelled with a suitable reporter molecule, such as a dye, enzyme, chemical catalyst, or a mixture of reagents capable of starting a chemical reaction that produces an optically or otherwise detectable signal indicating the presence of the analyte to be detected.

In one embodiment, said microparticle is specifically labelled.

In a further aspect, the present invention also relates to a collection of microparticles, said microparticles being as defined above.

In one embodiment, said microparticles are different from each other in that they are specific for different analytes to be detected, wherein each microparticle is specifically labelled such that different microparticles and their corresponding detected analytes can be distinguished by the specific labels of the microparticles.

In a further aspect, the present invention relates to the use of a microparticle according to the present invention or of a collection of microparticles according to the present invention, for performing a digital detection of an analyte or a plurality of analytes in a sample.

In a further aspect, the present invention relates to the use of a microparticle according to the present invention or of a collection of microparticles according to the present invention for enriching and concentrating an analyte in a defined volume, or for enriching and concentrating a plurality of analytes in a plurality of defined volumes, wherein preferably, all of said defined volumes in said plurality of defined volumes are equal.

In a further aspect, the present invention relates to a method of performing a digital detection of an analyte in a sample, said method comprising the steps:
a) providing a collection of prefabricated microparticles according to the present invention,
b) exposing said collection to a sample suspected of containing an analyte to be detected, thus allowing the capture agent to selectively and specifically bind the analyte to be detected, if present; wherein, optionally, after the step of reconstituting and/or the step of exposing, there is one or several washing steps;
c) placing the collection of microparticles into a non aqueous phase, e.g. an oil phase, and
either
d1) detecting the detection agent bound to said analyte or to said complex between said capture agent and said analyte; or
d2) amplifying the analyte, if present, by way of an amplification reaction, and detecting the thus amplified product by means of said detection agent, wherein said analyte is a nucleic acid and said amplification reaction is a nucleic acid amplification such as, for example, PCR, TMA, NASBA, LAMP, 3SR, SDA, RCA, LCR, RPA, NEAR, or
d3) performing a signal amplification reaction, e.g. a nucleic acid amplification if a nucleic acid is or forms part of said detection agent, or e.g. an enzyme-based amplification of a signal, e.g. in the form of a label, such as a dye or fluorophor, if an enzyme is or forms part of said detection agent, and detecting the thus amplified signal.

In one embodiment, in step a), said prefabricated microparticles are provided in dried form, and, in step b), said prefabricated microparticles are reconstituted in aqueous solution and then exposed to a sample suspected of containing an analyte to be detected.

In one embodiment, in step b) the number of microparticles and the number of analyte molecules in the sample are maintained or adjusted, as necessary, such that the binding of a single analyte molecule per microparticle follows a Poisson distribution, preferably such that, on average, there is no more than one analyte molecule bound per microparticle, thus allowing the detection of a single analyte molecule per microparticle.

In one embodiment, during step c), the collection of microparticles is suspended in the non-aqueous phase and/or is located on a solid substrate isolating each micro particle from other microparticles, wherein, preferably, said solid substrate is a filter, a sieve, a substrate having a pattern of wells, recesses, grooves, channels, trenches, craters, holes, pillars or any combination of the foregoing.

In one embodiment, during or after step c), the gel-forming agent is liquefied, preferably through the application of heat or light, or by a change of pH, redox potential, ionic strength, temperature, magnetic field or electromagnetic radiation, or upon exposure to an enzyme or, if the gel-forming agent itself comprises an enzyme, to a substrate of such enzyme, or any combination of the foregoing, resulting in an aqueous droplet in a non-aqueous phase.

In a further aspect, the present invention also relates to a method for making a prefabricated microparticle in accordance with the present invention, wherein said method comprises
a) providing, in any order, an aqueous phase including a gel-forming agent, and separate from said aqueous phase, an oil phase,
b) forming aqueous droplets of the aqueous phase including the gel-forming agent within the oil phase, preferably by generating a stream of the oil phase and by dosing in defined volumes of aqueous phase into said flowing stream of said oil phase,
c) collecting the thus generated aqueous droplets within said oil phase and subsequently separating said aqueous droplets from said oil phase by mechanical separation, such as centrifugation, sieving or filtering.

The present inventors have devised a methodology wherein, in contrast to the prior art, prefabricated microparticles are used in and for a method of performing a detection, in which said prefabricated microparticles themselves define and limit the reaction space in which said detection takes place. In other words, in accordance with embodiments of the present invention, the prefabricated microparticle(s) is (are) provided and is (are) used as a detection compartment. Thus, the dimensions of the microparticle(s) of the present invention define and limit the dimensions of said compartment in which a detection takes place. In contrast thereto, according to the prior art, in many instances, solid beads are used in which capture agents are attached to the surface thereof, and these beads themselves act to catch, immobilize or capture an analyte, but for a subsequent detection reaction these beads or particles are incorporated in droplets or reaction spaces which are considerably larger than said beads or particles. In contrast thereto, in accordance with embodiments of the present invention, a prefabricated microparticle itself defines and limits the dimensions of the reaction space in which a detection reaction takes place. Thus, the dimensions of the prefabricated microparticle in accordance with the present invention are the dimensions of the reaction space in which detection of an analyte takes place. Without wishing to be bound by any theory, the present inventors therefore consider their methodology as the first and only microparticle-mediated compartmentalization for a detection reaction. This distinguishes the present invention from all of the prior art methodologies described above. Thus, in accordance with embodiments of the present invention, the prefabricated microparticle, after having been exposed to an aqueous sample suspected of containing an analyte to be detected, is subsequently not incorporated in a larger aqueous droplet surrounded by an oil phase. Likewise, in accordance with embodiments of the present invention, the prefabricated microparticle after having been exposed to an aqueous sample suspected of containing an analyte to be detected, is also not placed into a larger compartment, such as a well or microreactor where it is combined with other constituents of an aqueous solution, including a volume of water, to form an aqueous droplet that is considerably larger than the microparticle itself. Instead, in accordance with embodiments of the present invention, the prefabricated microparticle itself defines and limits the reaction space/reaction compartment in which detection of an analyte takes place.

Hence, in accordance with embodiments of the present invention, the prefabricated microparticle(s) of the present invention provides a volume-defining scaffold which is or becomes filled with a aqueous solution to such an extent that the total void volume of said prefabricated microparticle is filled, or only a fraction thereof. In other words, in accordance with embodiments of the present invention, the total volume of the reaction space in which the detection of an analyte takes place, is limited at the upper end by the maximum volume provided for by the prefabricated microparticle and is factually limited by the total volume of liquid or liquid sample taken up by said prefabricated microparticle. Upon incorporation of said liquid-filled prefabricated microparticle in a non-aqueous phase, the liquid-filled volume of said prefabricated microparticle thus represents and acts as a reaction space in which a detection reaction of the analyte takes place.

Such a compartmentalization of a reaction space by way of a prefabricated microparticle which itself acts as a volume scaffold to provide for such reaction space, has not been described before.

Micro-droplet generating devices for performing such methods and for generating aqueous droplets do exist and may be readily adapted to the present invention. For example, devices that are useful for the present invention are dosing devices from Dolomite Microfluidics, UK. Such devices are also further described in WO 2002/068104 and WO 2005/089921. The devices described therein can be adapted to generate aqueous microdroplets within an oil phase, in accordance with embodiments of the present invention. In a further embodiment, the separated aqueous droplets generated by the above method, in particular after step c) can be washed using an aqueous solution or water. Furthermore, subsequently, they can be dried, e.g. freeze-dried. In accordance with the present invention, the aqueous droplets thus produced are prefabricated microparticles in accordance with the present invention. In one embodiment, a gel forming agent may be used for forming the aqueous droplets/prefabricated microparticles, and such gel-forming agent is as defined further above. In one embodiment, the aqueous droplets including the gel-forming agent are dried, preferable freeze-dried. Alternatively, any other suitable means of stripping off the solvent may be employed. Once the solvent has been removed and the aqueous droplet/produced microparticle has been dried, it may be stored as a powder. The present inventors have surprisingly found that by providing prefabricated microparticles in accordance with the present invention, it is possible to provide miniaturized and defined reaction spaces that may be used in a very versatile manner for detection reactions, for example for performing a digital detection of an analyte in a sample. The prefabricated microparticles, in accordance with embodiments of the present invention, may be tailor made by choosing an appropriate capture agent that is comprised by the prefabricated microparticle and that, upon exposure of the microparticle to a sample that surrounds the microparticle and that contains an analyte, selectively and specifically binds the analyte to be detected. Because of their defined size, the microparticles take up a defined volume of liquid and thus allow any (detection) reaction to take place in a defined volume of liquid. Effectively, the particles provide an efficient and easy means to portion a sample suspected of containing an analyte to be detected into well and clearly defined small volumes. The microparticles in accordance with embodiments of the present invention also provide an easy means to selectively enrich and/or concentrate the analyte to be detected selectively on the surface of the microparticle. If desired, they furthermore allow the achievement of a uniform and standardized concentration of analyte stemming from different samples having different volumes and different starting concentrations of analyte. Different microparticles may be specific for different analytes to be detected by choice of appropriate capture agent (s). Moreover, depending on their respective specificity for an analyte to be detected, different microparticles, in accordance with embodiments of the present invention, may be specifically labeled such that different microparticles and their corresponding detected analytes can be distinguished by the specific labels of the microparticles. Such specific labelling and the distinction that can be achieved thereby is herein also sometimes referred to as "encoding". An "encoded" microparticle is a microparticle that has been made specific, in terms of its binding capabilities, for a particular analyte and that has also been marked or labelled specifically accordingly. According to one embodiment, the prefabricated microparticles are made of a gel-forming agent. In one embodiment, the gel-forming agent may exist in two different states, one state being a solid state or semi-solid state, the other state being a liquid state. In one embodiment, in the solid state or semi-solid state, the gel-forming agent is present in the form of a gel which forms a matrix, and, with such gel, the microparticles may, for example, be in the form of a suspension wherein the microparticles include a volume of an aqueous solution and are dispersed in a non-aqueous medium, such as an oil medium. Effectively, in this state, the microparticles represent aqueous droplets that are reinforced by a matrix formed by the gel-forming agent/gel. As outlined further above, such matrix defines the surface and the void volume of the microparticle. In a further embodiment, the gel-forming agent may be transferred from the solid/semi-solid state into a liquid state upon the application of an appropriate stimulus. Such stimulus may be for example the application of heat or light or it may involve a change of pH, redox potential, ionic strength, temperature, magnetic field or electromagnetic radiation. Alternatively, such external stimulus may also be the exposure to an enzyme (which, for example, may digest the matrix formed by the gel-forming agent), or, if the gel-forming agent itself comprises an enzyme, such stimulus may be exposure to a substrate of such enzyme. Also combinations of any of the foregoing stimuli are envisaged. Once the gel-forming agent has been transferred from the solid/semi-solid state to a liquid state, there will result an aqueous droplet in a non-aqueous medium (e. g. oil). As long as the gel-forming agent is in the solid/semi-solid state, the microparticles are in the form of a suspension of such solid/semi-solid particles in a non-aqueous phase. Once the gel-forming agent has been liquefied, the microparticles are in the form of an emulsion of an aqueous phase in a non-aqueous phase.

The prefabricated microparticles in accordance with embodiments of the present invention are storable, in particular in a dry state or dried state, preferably for a period of at least two months, more preferably for a period of at least six months. In one embodiment, they are storable for a period of at least one year. In one embodiment, the prefabricated microparticle according to the present invention may comprise one or several stabilizing agents helping to preserve the microparticle. Examples of such stabilizing agents are cyclodextrins (e.g. Cavasol®), trehalose, sucrose, lactose, mannose, glucose, galactose, mannitol, myoinositol, poly(alkylene oxides), in particular poly(ethylene glycols) and their derivatives. The term "prefabricated", as used herein, is meant to differentiate the microparticle/microparticles according to the present invention from other microparticles from the prior art which may possibly be used for detection purposes, in that the prefabricated microparticle(s) in accordance with the present invention is (are) not a particle (particles) that is (are) generated at the time and/or place of its (their) intended use. Hence, a prefabricated microparticle according to the present invention is not an in-situ generated particle, i. e. it is not a particle that is generated in the course of the reaction, e. g. the analytic assay, in which it is intended to be used. In particular, it is not generated at the site or time or reaction at, in or during which an analyte detection is to take place. The term "in-situ generated", as used herein, is meant to refer to a substance or particle that is generated from one or more precursors at the place and/or time of intended use of such substance or particle. Moreover, a prefabricated microparticle, in accordance with the present invention, is not a particle that, at the time of its being generated, is made to encompass or include or incorporate or engulf a sample containing an analyte. Rather, a prefabricated microparticle in accordance with the present invention is generated first and, optionally, further processed, e. g. washed, dried, reconstituted etc.; and only after its generation, a prefabricated microparticle according to the present invention then is exposed to a sample containing an analyte or suspected of containing an analyte.

The term "microparticle", as used herein, is meant to refer to a particle the average dimensions of which are in the micrometer range. In one embodiment, the microparticles in accordance with the present invention have an average size or average dimension or average diameter of approximately 5 µm-200 µm, preferably 5 µm-150 µm, more preferably 10 µm-100 µm. In one embodiment, the microparticles in accordance with the present invention are spherical or oval or ellipsoidal, preferably spherical, and the above-mentioned dimensions refer to the average diameter of such spherical, oval or ellipsoidal microparticle. In one embodiment, the microparticles have the shape of a (spherical) droplet. In another embodiment, a microparticle in accordance with the present invention is a spherical body or a quasi-spherical body, i. e. having the shape of a sphere (or nearly approaching it), such sphere having an average diameter of the aforementioned dimensions. In one embodiment, a microparticle in accordance with the present invention is porous. In a further embodiment, a microparticle in accordance with the present invention, in particular a porous microparticle, has a surface that is available for accommodating a capture agent, in that the capture agent is predominantly located on the surface of the microparticle. In one embodiment, the surface of a porous spherical microparticle in accordance with the present invention having a defined diameter, is x-times the surface of a non-porous microparticle having the same diameter, with x being selected from at least 2, at least 5, at least 10, at least 50, at least 100 or at least 500. In such a porous spherical microparticle in accordance with the present invention, the density of capture agent per microparticle is greatly enhanced and allows for a particularly efficient concentration of analyte to be detected at the surface of the microparticle. This is because the density of capture agent on the surface of the microparticle is also particularly high.

The microparticle(s) in accordance with embodiments of the present invention are also characterized by the fact that, when being generated or when in use, they do not incorporate or include or encompass a biological cell. Likewise, when being generated or when in use, they also do not include or incorporate or encompass an analyte in their interior. Rather, any analyte that is to be detected by means of the prefabricated microparticle according to the present invention is selectively and specifically bound by the prefabricated microparticle at its surface, with the analyte being located in or stemming from a sample surrounding the prefabricated microparticle. Hence, in one embodiment, the microparticle according to the present invention comprises a capture agent that, upon exposure of the microparticle to a sample surrounding the microparticle and containing an analyte, selectively and specifically binds the analyte to be detected, wherein the capture agent binds the analyte from a sample surrounding the microparticle (and does not bind an analyte from a sample that is located within the particle). In one embodiment, the microparticle comprises a capture agent that is predominantly located on the surface of the microparticle, and consequently, the microparticle is thus capable of enriching and concentrating an analyte located outside of the microparticle. The term "predominantly located", when used in conjunction with a capture agent being located on the surface of a microparticle, is meant to refer to a scenario wherein the majority of such capture agent molecules are located on the surface of the microparticle rather than in its interior. As used herein, the term "surface" is meant to refer to the part of a microparticle that is accessible from the outside of the microparticle. Likewise, as used herein, the term "interior of a microparticle" is meant to refer to the part of a microparticle that is not accessible to the outside of the microparticle. In one embodiment according to the present invention, the microparticle according to the present invention does not encapsulate or encompass an analyte or a biological cell or a microorganism, such as a bacterium, and hence does not contain such analyte in its interior.

In accordance with embodiments of the invention, a microparticle will have an inherently (limited) capability of comprising or accommodating a capture agent. Hence, in one embodiment of a collection of microparticles, preferably, the individual microparticles will have approximately the same density of capture agents, i. e. the same number of capture agents per unit surface of microparticle. This will allow the microparticles to enrich and concentrate an analyte to approximately the same concentration, even when different samples having different concentrations of analyte, are used. Thus, the prefabricated microparticles according to embodiments of the present invention also allow the generation of multiple identical reaction spaces/volumes, preferably with a uniform concentration of analyte at the surface of the microparticles, after the microparticles have been exposed to a sample containing an analyte.

As used herein, the term "digital detection", when used in conjunction with microparticles according to the present invention, is meant to refer to a scenario wherein either the ratio of the number of microparticles to the number of analyte molecules is adjusted such that there is maximally a single analyte molecule bound per microparticle and the binding of a single analyte molecule per microparticle follows a Poisson distribution. Alternatively or additionally the term "digital detection" when used in conjunction with microparticles according to the present invention, is meant to refer to a scenario wherein a sample is portioned by means of a collection of microparticles according to the present invention such that each microparticle provides the same reaction volume and reaction conditions and, preferably also contains approximately or exactly the same number of analyte molecules. In the latter scenario, the microparticles thus serve to create a plurality of like reaction spaces (e. g. detection spaces) for each analyte type to be detected, in which reaction spaces preferably the individual concentrations of analyte are the same (or nearly identical within the error margin) amongst different microparticles. Thus the microparticles, in accordance with embodiments of the present invention, allow for the generation of a plurality of identical reaction micro-spaces in which for each type of microparticle, preferably, identical or nearly identical analyte concentrations and/or reaction conditions are achieved. The latter scenario is of particular interest under conditions when the concentration of the analyte in a sample is sufficiently high. The former scenario (1 analyte bound per microparticle at a maximum) is particularly applicable when the concentration of the analyte in a sample is rather low. In one embodiment, the present invention also relates to the use of prefabricated microparticles as defined further above, for the provision of a plurality of identical or nearly identical reaction spaces, providing identical reaction volumes and identical reaction conditions, e. g. for performing a detection reaction.

In one embodiment, in a collection of prefabricated microparticles according to the present invention, all the microparticles are of identical size and thus, each of such prefabricated microparticles provides for and defines the same reaction volume, such reaction volume for example serving as reaction space for a detection reaction. In one embodiment, in a collection of prefabricated microparticles according to the present invention, all microparticles are of the same type and are specific for the detection of one analyte. In another embodiment, in such collection of prefabricated microparticles according to the present invention, there are different types of microparticles with each type being specific for the detection of a different analyte. The latter collection of microparticles according to the present invention is particularly useful for the detection of multiple (different) analytes in one or several samples. Sometimes, as used herein, the term "prefabricated microparticle" is used herein interchangeable with the term "digital amplification beads" (abbreviated also as "DAB"). In one embodiment, in a collection of prefabricated microparticles according to the present invention, such prefabricated microparticles exist as entities that are spatially totally separate from each other. In one embodiment, in such collection of prefabricated microparticles according to the present invention, such collection is therefore mono-disperse. If necessary, such collection of mono-disperse prefabricated microparticles may be provided with the prefabricated microparticles being located on or associated with a substrate. For example, such substrate may be a sieve with individual wells providing just enough space to accommodate a single prefabricated microparticle per well. Alternatively, such substrate may be a substrate with regularly arranged recesses or channels or grooves for accommodating a prefabricated microparticle each. In one embodiment, such substrate may be a filter. In one embodiment, the prefabricated microparticles, containing an aqueous solution and being dispersed/suspended in a non-aqueous phase may be subjected to one or several washing steps. To this extent, they may also be kept on a substrate of the aforementioned kind. Alternatively and/or additionally, the prefabricated microparticles according to embodiments of the present invention may subsequently be exposed to a sample containing an analyte or suspected of containing an analyte. By virtue of a suitable capture agent being present on a prefabricated microparticle, an analyte stemming from a sample surrounding the microparticle, may be bound to the microparticle and may subsequently be detected. The purpose of the capture agent is a local concentrating and enriching of analyte on the outside of the microparticle. The purpose of the detection agent is to bind the analyte or a complex between a capture agent and the analyte, and to thus make such analyte, alone or in complex with a capture agent, detectable. In one embodiment, such detection occurs by either detecting the detection agent which is bound to the analyte or to the complex between the capture agent and the analyte. In another embodiment, the analyte is amplified by way of an amplification reaction, and the thus amplified product is detected by means of the detection agent, this being particularly preferred in the case that the analyte is a nucleic acid and the amplification reaction is a nucleic acid amplification reaction. Examples of such nucleic acid amplification reactions are polymerase chain reaction (PCR), transcription-mediated amplification (TMA), nucleic acid sequence-based amplification (NASBA), loop-mediated isotheinial amplification (LAMP), self-sustained sequence replication (3 SR), strand displacement amplification (SDA), rolling circle amplification (RCA), ligase chain reaction (LCR), recombinase polymerase amplification (RPA), and nicking enzyme amplification reaction (NEAR). A person skilled in the art is well aware of any of these amplification reactions and is capable of performing these, as necessary. In a further embodiment, detection of the analyte may occur by performing first a signal amplification reaction and subsequently detecting the thus amplified signal. In the latter embodiment, a signal is only amplified if there is a signal in the first place, that is, a signal only occurs when there is an analyte to be detected, and the signal amplification reaction may for example be a nucleic acid amplification if a nucleic acid is or forms part of the detection agent. Alternatively, the signal amplification reaction may be an enzyme-based amplification of a signal, if an enzyme is or forms part of the detection agent.

In a preferred embodiment of the method of performing a digital detection of an analyte in a sample, a collection of prefabricated microparticles according to the present invention are exposed to a sample suspected of containing an analyte to be detected, and in such step of exposure, the number of microparticles and the number of analyte molecules in the sample are maintained or adjusted, as necessary, such that the binding of a single analyte molecule per microparticle preferably follows a Poisson distribution. In a preferred embodiment of this method, on average, there is no more than one analyte molecule bound per microparticle. This allows the detection of a single analyte molecule per microparticle. In another embodiment, the number of analyte molecules per microparticle is maintained or adjusted, as necessary, such that, on average, in each microparticle there is an identical number of analyte molecules bound per microparticle. In this latter embodiment, the microparticles thus serve to create a plurality of like detection spaces for a detection reaction to take place.

Figure 1:
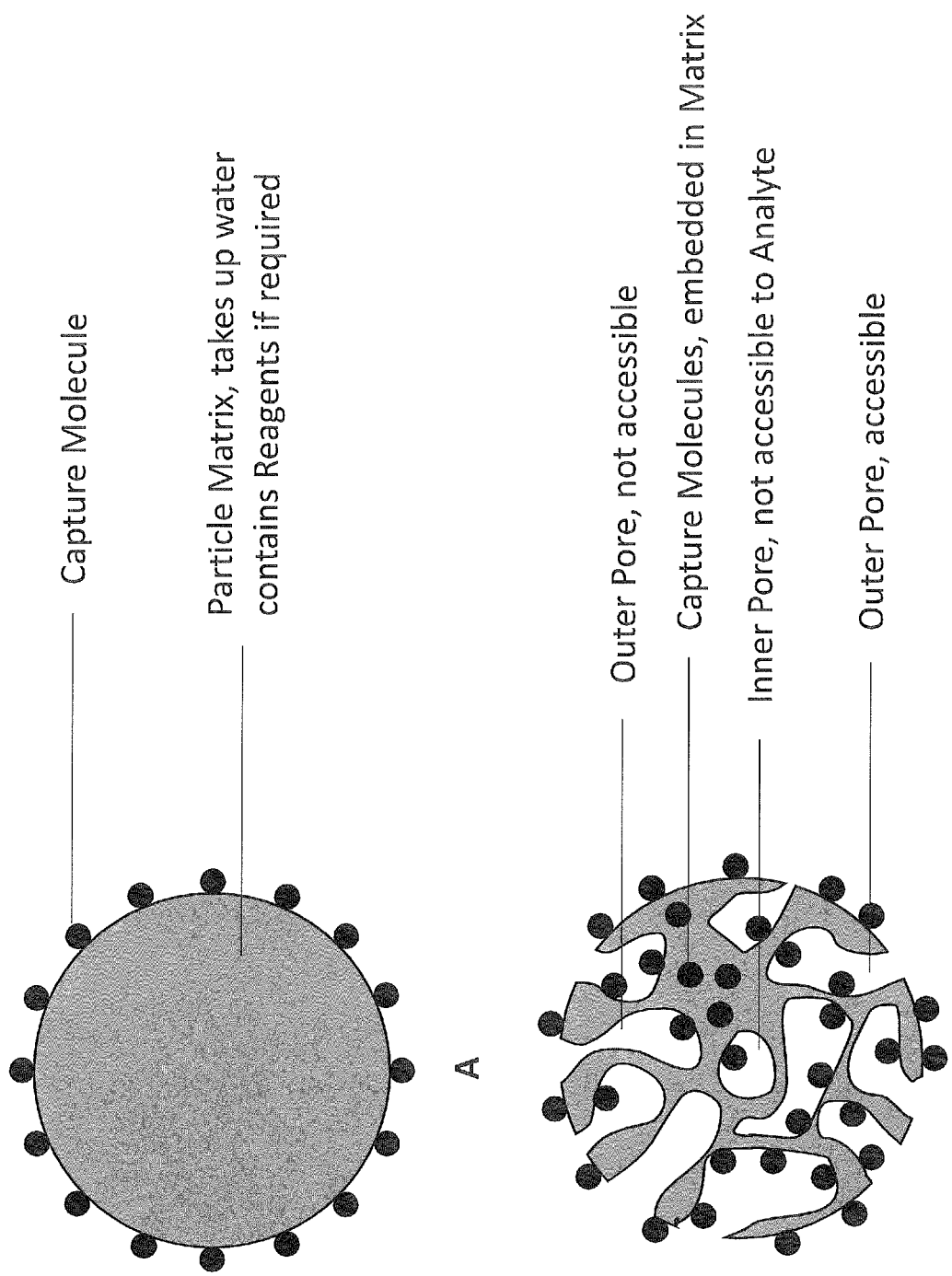
FIG. 1 shows a schematic representation of prefabricated microparticles in accordance with embodiments of the present invention. Panel A shows an outside view of a prefabricated microparticle (large grey circle) on which a number of capture agent molecules (small filled black circles) are immobilized. The prefabricated microparticle has a matrix that is capable of taking up an aqueous solution including reaction reagents for any reaction in which the prefabricated microparticle in accordance with the present invention is to be used. Panel B shows an embodiment of a prefabricated microparticle which has pores. Panel B shows an embodiment wherein the prefabricated microparticle according to the present invention is porous having a number of pores, some of which are accessible from the outside and some of which are not. Again, the capture agent molecules are shown as small filled black circles. The capture agent molecules are predominantly located on the surface of the microparticle, such surface referring to the part of the microparticle that is accessible from the outside of the microparticle. In accordance with embodiments of the present invention, such twin "being accessible" is meant to refer to accessibility by or for an analyte to be detected. The prefabricated microparticles in accordance with the present invention may be used in detection or quantitation reactions, for example a digital detection reaction.
Figure 2:
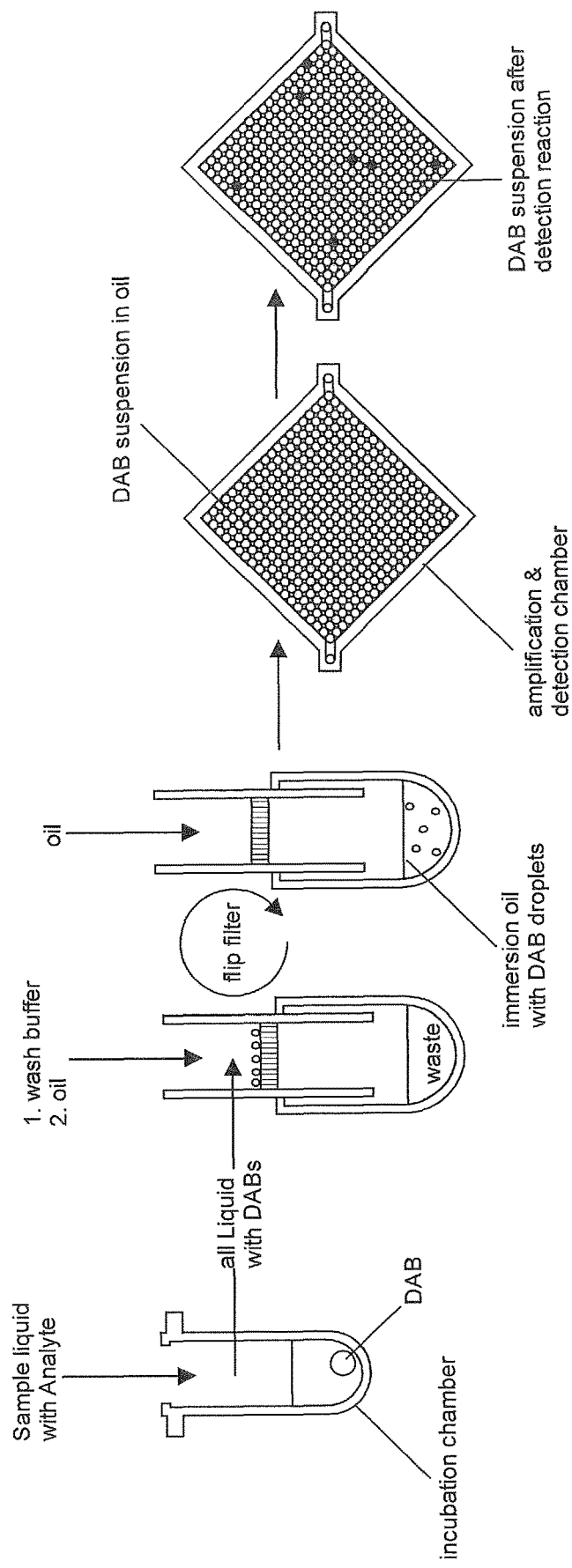
FIG. 2 shows a schematic flow diagram of a detection reaction in accordance with the present invention. To a vessel containing prefabricated microparticles according to the present invention (such prefabricated microparticle being schematically shown in the figure as a white circle at the bottom of the reaction vessel), there is added a sample liquid including an analyte. The prefabricated microparticle in accordance with the present invention (herein also sometimes referred to as digital amplification bead, "DAB") after having been exposed to the (optionally labelled) analyte and after having bound the analyte by the capture agent, is transferred to a new reaction vessel. The prefabricated microparticles according to embodiments of the present invention comprise a suitable capture agent, e. g. streptavidin, that is capable of binding the analyte of interest, in the present example the biotinylated analyte of interest. The prefabricated microparticles according to the present invention are placed on a sieve or filter on top of the reaction vessel and washed with an appropriate wash buffer in order to remove unbound analyte. The prefabricated microparticles in accordance with the present invention will thus contain an aqueous solution and, if the capture agent of the prefabricated microparticles according to the present invention have bound the analyte, also the corresponding analyte on the surface. Thereafter, the prefabricated microparticles according to the present invention, resting on the sieve or filter are immersed in an oil phase, e. g. an immersion oil. Thereafter, the sieve or filter is turned upside down, and the prefabricated microparticles containing an aqueous phase including the analyte are washed with further immersion oil to produce a suspension of prefabricated microparticles (containing an aqueous solution including an analyte) in an oil phase, in the present case the immersion oil used for washing of the prefabricated microparticles from the sieve or filter. The microparticles in accordance with embodiments of the present invention also contain a detection agent allowing the detection an analyte in a subsequent detection reaction. Such subsequent detection reaction is then performed as a result of which certain microparticles indicate the presence of an analyte, whereas others do not. Those microparticles indicating the presence of an analyte are shown in the figure as dark filled circles, whereas those microparticles indicating a negative result are shown as white circles.
Figure 3:
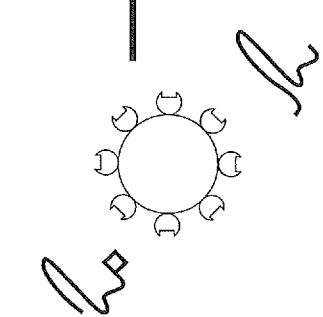
FIG. 3 shows a similar reaction to the reaction shown in FIG. 2, but at the level of the individual microparticle. On the left, there is shown a prefabricated microparticle in accordance with embodiments of the present invention, such microparticle being shown as a white circle. There are capture agent molecules located predominantly on the surface of the microparticle, and on the outside surrounding the microparticle, there are nucleic acids (squiggly lines) some of which are labeled with a suitable agent, e. g. biotin (square). The capture agent molecules comprise another complementary agent, e. g. streptavidin (negative mold of a square shown on the capture agent, "pearls" decorated on the surface of the microparticle) in this embodiment, and those nucleic acids labeled with biotin (square) will bind to the respective capture agents. It is clear that biotin and streptavidin may also be exchanged, i. e. the biotin is comprised by the capture agent, and the streptavidin is attached to the nucleic acid. Unlabeled nucleic acids will not bind and can be washed off in a subsequent wash step (see FIG. 2). The respective microparticle containing solution is then mixed with oil and any aqueous liquid not embedded in a particle is removed from the oil phase. Thus remains a suspension of particles in an non-aqueous matrix (shown in the figure as a square frame). The material from which the prefabricated microparticle in accordance with the present invention is made can also be liquefied in this embodiment, and if such liquefication occurs (see right square frame of the figure), after the microparticle has been put into an appropriate oil phase, this will generate a microreaction space containing an aqueous solution including an analyte to be detected and a detection reaction within an oil phase (right hand square frame in FIG. 3).
Figure 3:
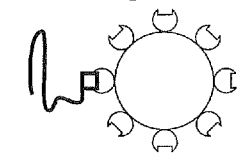
Figure 3:
Figure 4:
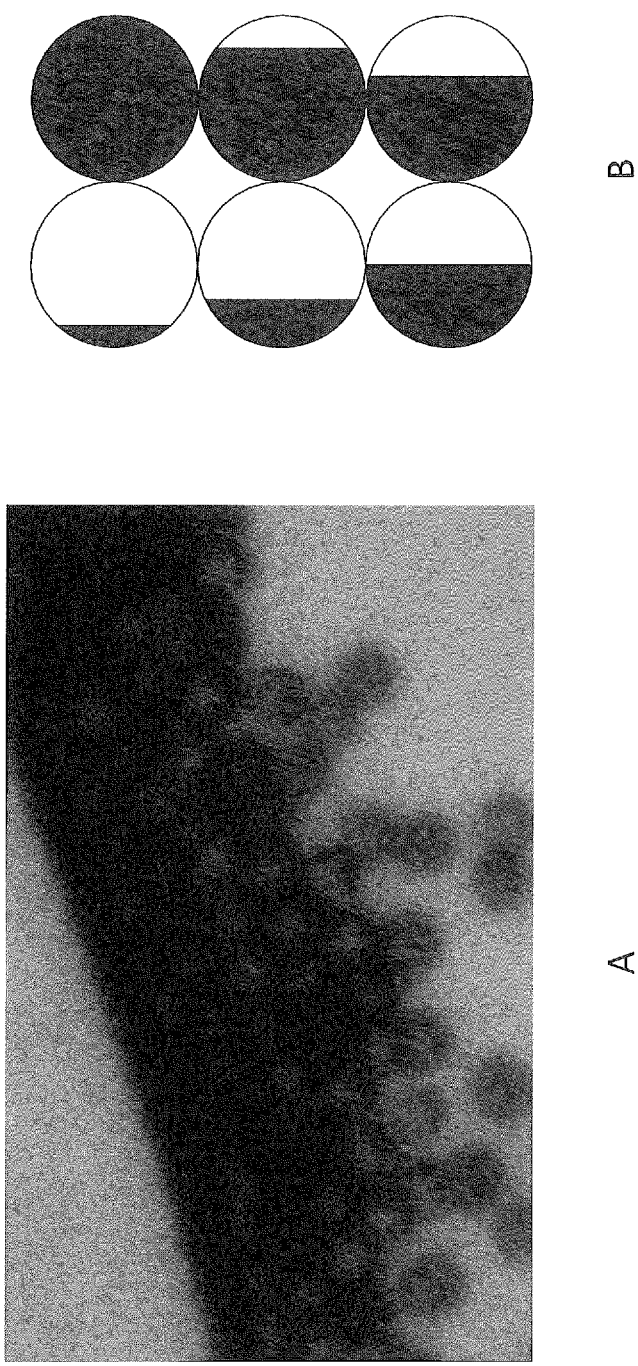
FIG. 4 shows different colour-coded/labeled prefabricated microparticles (or digital amplification beads, "DABs") which have been marked with different dyes. Such different labels may be achieved by either choosing different dye types or different dye concentrations for different prefabricated microparticles. On the right hand panel (B), this is schematically shown by showing different microparticles according to the present invention which have different amounts of dye and which are specific for different analytes. Such "encoding" may be in relation to the specificity of the capture agent or the specificity of the detection agent of the individual microparticle.
Figure 5:
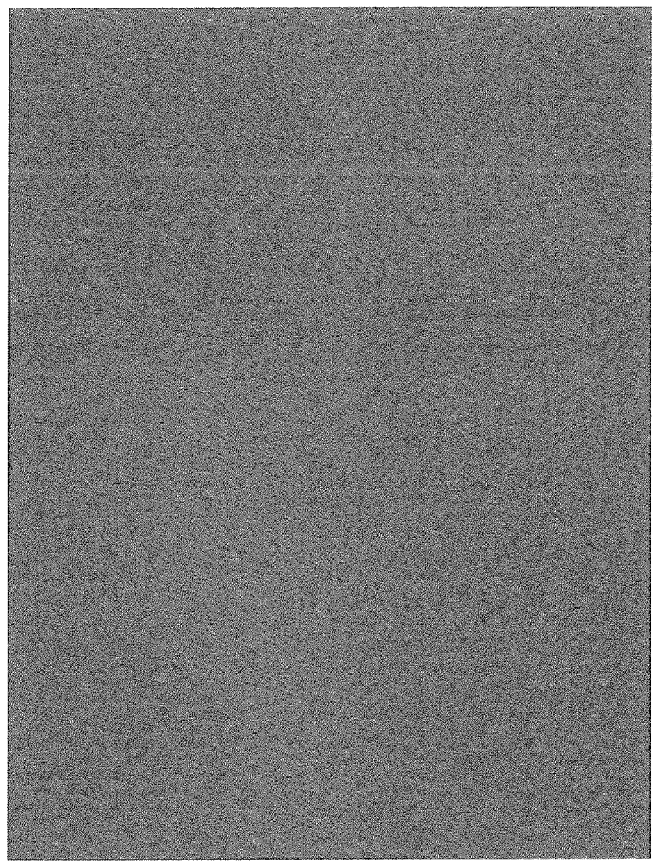
FIG. 5 shows examples of prefabricated microparticles in accordance with the present invention. Panel A shows a 5× magnified transmission image of prefabricated microparticles containing an aqueous phase in an oil phase. Panel B shows a 5× magnified transmission image of prefabricated microparticles containing an aqueous phase, in phosphate buffer saline solution (PBS). In both panels, it can be seen that the prefabricated microparticles are uniform in size and provide a plurality of identical reaction volumes/reaction spaces for a detection reaction to take place.
Figure 5:
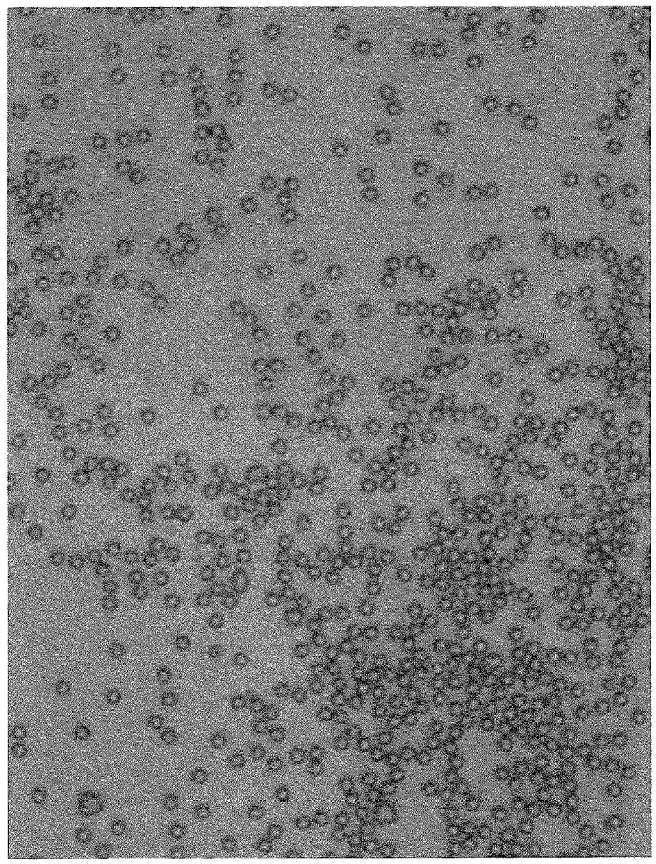
Figure 6:
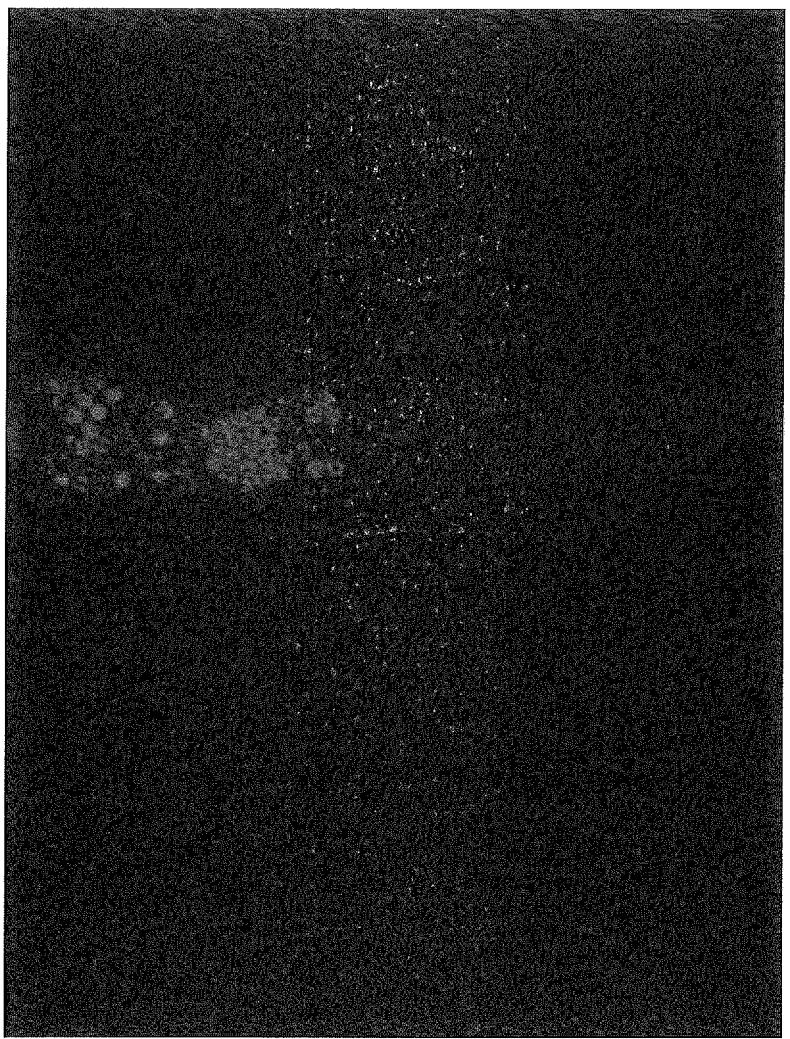
FIG. 6 shows a 5× magnified fluorescence image (with an excitation wave length of 490 nm and an emission wave lengths of 510 nm) wherein prefabricated microparticles in an oil phase are shown after a PCR-amplification reaction has been performed. The prefabricated microparticles were produced as described in embodiment 2 of the examples of the present specification. As can clearly be seen there are prefabricated microparticles which have a bright fluorescence signal, and there are other prefabricated microparticles which show a low flow fluorescence signal. In those microparticles with a bright fluorescence signal, a successful amplification of the analyte, in this case of a nucleic acid, has taken place, and this is shown by the bright fluorescence signal. In other microparticles, no amplification reaction has taken place, and this is indicated by no fluorescence or by a comparatively low(er) fluorescence signal which stems from the background fluorescence of the probes that have been used here (e.g. TaqMan probes).

Moreover, reference is now made to the following specific examples which are given to illustrate, not to limit the present invention.

EXAMPLES

Embodiment 1: Generation of Mono Disperse Digital Amplification Beads (DABs)

Generation of DAB Mixes
Component 1:
Deionized Water, nuclease free
Ultra low gelling Agarose (Sigma-Aldrich, #A5030), biotin-labelled 2% (w/v)

In order to prepare biotin-labeled agarose, the Ultra-low Gelling Temperature Agarose was first activated and then coupled to EZ-Link™ Amine-PEG11 biotin. The activation can alternatively be carried out by bromine cyan modification, mild oxidation (generation of aldehyde groups), carbonyldiimidazole (CDI), a di- or trichlorotriazine compound or by other methods known. Alternatively, a reactive biotin compound such as, for example, a biotin-monochlorotriazine can be coupled directly onto agarose. Optimal biotin coverage is determined by titration in preliminary tests in order to maximize streptavidin binding capacity while maintaining the matrix properties of agarose (melting and gel formation behavior, low unspecific binding).

The constituents of component 1 are pipetted together, shaken briefly on a vortex mixer and centrifuged. Subsequently, the mixture is incubated at 65° C. at 1500 rpm in a thermoshaker in order to melt the ultra-low gelling agarose and obtain a homogeneous agarose amplification mixture. Subsequently the component 1 mixture is cooled down to 35° C. and mixed with an equal volume of component 2 that has been kept at the same temperature.

Component 2 consists of 2× Platinum™ Hot Start PCR Master Mix (Invitrogen, #13000012. The DAB mixture is then kept at 35° C. until further use.

Generation of Mono Disperse DABs on the Dolomite µEncapsulator System 5 mL of the emulsion reagent PicoSurf™ 5% in Novec7500 oil (Dolomite Microfluidics) are filtered through a 0.2 µm filter, transferred to a clean 20 ml glass tube (Fisher Scientific, #12353317) and placed into the reservoir of a pump controlling the flow of the oil phase (oil phase pump). Two other pumps controlling the flow of the agarose phase (DAB mix pumps) are filled with the inert "driving liquid" HFE-7500 (Dolomite Microfluidics, #3200425).

A "Reagent Droplet Chip" (50 µm, fluorophilic Dolomite Microfluidics, #3200445) and a "Sample Reservoir Chip" (Dolomite Microfluidics, #3200444) are placed in the µEncapsulator 1 system. The set temperature of the Temperature control unit (TCU) is set to 35° C. A volume of 100 µl of the DAB mix is added to each reservoir of the sample reservoir chip. Droplets are generated with flow rates of approx. 2 µl/min for both DAB Mix pumps and with approx. 50 µl/min for the oil phase pump. The parameters are monitored with the Dolomite Flow Control Advanced Software. The generated DABs have a volume of approx. 65 µl. The material is collected in an Eppendorf tube on ice, and then stored at 2-8° C.

Transfer of DABs to the Aqueous Phase and Exclusion of Non-Compliant Particles

The DABs are extracted from the oil phase by centrifugation through a sieve structure. Thus beads of deviant size are removed. For this purpose, the DAB emulsion is first applied to a tube equipped with a SEFAR PETEX® fabric w=44 µm) and centrifuged at 300×g. The oil phase and under-sized DABs are moved through the sieve while larger DABs remain on the SEFAR fabric. In order to completely remove the oil phase, the DABs are re-suspended in wash buffer and filtered again through the SEFAR sieve. The employed wash buffer consists of 1× Taq DNA polymerase PCR buffer [20 mM Tris HCl (pH 8.4), 50 mM KCl] (Invitrogen, #18067017) and 1% TritonX100 (Sigma-Aldrich, #X100). This washing step is repeated 5 times until the oil phase has been completely removed. Two additional washing steps are performed with 1× Taq DNA polymerase buffer without detergent. DABs are recovered by applying the filter unit into a suitable centrifuge tube in opposite orientation. Wash buffer is applied from the top onto the back side of the filter (the side facing away from the particles). The filtration unit is centrifuged for 1 min at 1.000×g. In order to recover all particles this step is repeated several times. Over-sized DABs are filtered out by pipetting the entire volume onto a filter equipped with SEFAR PETEX® tissue with a mesh width of w=59 µm (SEFAR AG, 07-59/33). The unit is briefly centrifuged at 300×g. Material that has passed the filter is collected and contains the DABs of the desired size.

Coating of DABs with Streptavidin

Coating of the DABs with streptavidin is accomplished in the washing buffer used before. The concentration of streptavidin is selected such no accessible biotin remains on the surface of the DABs. In any case Streptavidin is applied in excess in order to avoid cross-linking of DABs. Optimal streptavidin concentration has been determined in preliminary tests with labelled Streptavidin by determining a plateau surface coverage. After coupling with Streptavidin the DABs are washed several times on 44 µm SEFAR PETEX centrifugation units with a wash buffer without Streptavidin. Subsequently, the concentration of the DABs is determined by counting under a microscope in a DHC-N01 (Neubauer Improved) counting chamber (INCYTO) or cytometrically on the CytoFlex flow cytometer (Beckman Coulter).

The DABs are aliquoted in units containing approximately 100,000 beads and mixed with 100 mM Trehalose. After excess buffer volume has been removed the DABs are lyophilized.

Embodiment 2: Application of Mono Disperse Amplification Beads (DABs) for Performing Digital PCR Enrichment of a HIV 1 (Subtype O) Targets on DABs and Incubation of Those Beads with a Amplification Mix Purified HIV-1 RNA (subtype O) labeled with biotin by reverse transcription is enriched on streptavidin-modified digital amplification beads. The entire volume of the reverse transcription reaction is added to a defined amount of lyophilized DABs. DABs absorb a part of the applied liquid and swell. The beads are carefully re-suspended. In order to avoid agglomerates ultrasound may be used. Subsequently the suspension is applied to a centrifugation tube equipped with SEFAR PETEX® tissue (w=44 μm). The supernatant is removed by centrifugation of the column at 300×g. For washing, the previously used wash buffer is added without detergent to the column and also centrifuged at 300×g. Washing is repeated several times and the DABs are ultimately taken up in component 3. In this embodiment the DABs take up all the components necessary for the PCR by diffusion.

Component 3 consists of the following reagents (final concentrations):

1× Platinum™ Hot Start PCR Master Mix (Invitrogen, #13000012)

0.2 μM sense primer: GCAGTGGCGCCCGAACAGG (Metabion international AG) (SEQ ID NO:1)

0.2 μM antisense primer 1: ACTGACGCTCTCGCACC-CATCT (Metabion international AG) (SEQ ID NO:2)

0.2 μM antisense Primer 2: TGACGCTCTCGCACC-CATCTCTC (Metabion international AG) (SEQ ID NO:3)

1× SYBR® Green I nucleic acid gel stain (Sigma-Aldrich, #S9430) or 1× EvaGreen®Fluorescent DNA stain (Jena Bioscience, #PCR-352)

Compartmentalization by Dispersing of DABs in Oil

Micro-compartments with a defined volume are created by dispersing DABs in a fluorocarbon oil, e.g. PicoSurf™ 5% dispersed in Novec 7500 oil (Dolomite Microfluidics, #3200214. Instead of a heavy fluorocarbon oil a light mineral oil with emulsifier, e.g. Mineral oil (Sigma-Aldrich, #M5904 Sigma) with 5% (w/w) Span 80 (Sigma Aldrich, #85548) may be applied.

The complete aqueous phase is brought in contact with an excess of oil in an Eppendorf tube. Ultrasound is applied for one minute. Both the DABs loaded with HIV-1 subtype 0 target and the supernatant of component 3 are dispersed and emulsified in the oil phase. The generated aqueous droplets of the supernatant of component 3 and the DABs differ significantly in their volume, the droplets having a much smaller volume. The generated emulsion is pipetted onto SEFAR PETEX® tissue with a mesh width of 44 μm. Smaller droplets as well as larger droplets that may not contain DABs are removed by mild centrifugation. Repeated washing with the same oil removes all liquid droplets. By introducing the filter unit into a suitable centrifuge tube in the opposite orientation the concentrated DABs are extracted from the sieve. The oil with the DABs is transferred into a detection chamber with an area of approximately 2 cm$^2$ and a layer thickness of approximately 1 mm. The opposite surfaces of the chamber are made of transparent hydrophobic material. If a fluorocarbon oil is used, the DABs assemble as a monolayer (dense packing) on the hydrophobic upper surface due to the difference in density between the beads and the oil. If a mineral oil is applied the DABs will accumulate at the lower surface. Thus the DABs provide micro reaction containers for the subsequent digital PCR.

Amplification Reaction in DAB Micro-Compartments

DABs suspended in oil are subjected to the temperature cycling in the same chamber on a PELTIER element 30×30× 4.7 mm, 19.3 W (Quick-Ohm, Kiipper & Co. GmbH, #QC-71-1.4-3.7M). The captured cDNA is internalized upon melting of the agarose and transformation of DABs into liquid droplets. The amplification of individual cDNA molecules takes place in the resulting micro-reaction compartments.

The thermal conditions applied are:

Initial denaturation for 2 min at 95° C. followed by 45 cycles of Denaturation at 95° C. for 15 sec, Annealing at 65° C. for 15 sec and Extension at 72° C. for 30 sec. Upon completion or the thermal protocol the content of the chamber is imaged at 21° C. in transmitted white light and fluorescence mode with excitation λexc=470 nm and long pass emission of >496 nm. The total number of DABs and the number of those with a fluorescence signal above a defined intensity threshold are determined. The threshold value is derived from previously performed amplification reactions without template. The number of templates in the reaction is determined by applying the determined numbers of positive and negative droplets to Poisson statistics.

Embodiment 3: Establishing Digital ELISA

Here we describe the process of establishing a digital immunoassay for the detection of human cTnI. The assay employs immuno-PCR in a digital format: a DNA-labeled detection antibody and a streptavidin-labeled capture antibody form a sandwich complex with the antigen in solution. This complex is trapped on biotin-coated agarose particles with embedded reagents for carrying out a PCR amplification. Unbound detection antibody, and thus the DNA label, is removed by appropriate washing steps. The agarose particles are suspended in oil so that separate reaction compartments are formed. In the subsequent droplet PCR bound DNA-label is detected.

Detection Antibodies

The cTnI detection antibody (clone 3H9, SDIX) is labeled using the Thunder-Link® PLUS Oligo Conjugation System (Innova Bioscience) according to the manufacturer's protocol and then purified. The following sequence is coupled to the antibodies:

(SEQ ID NO: 4)
5'GCGTCAGACCCCGTAGAAAAGATCAAAGGATCTTCTTGAGATCCTTTT

TTTCTGCGCGTAATCTGCTGCTTGCAAACAAAAAAACCACCGCTACCAGC

GGTGGTTTGTTTGCCGGATCAAGAGCT3'

Capture Antibody:

Clone TPC-110 (SDIX) is used as a capture antibody. This was marked by Lightning link Streptavidin (Innova Bioscience) according to the manufacturer's protocol.

Preparation of DABs

Preparation of the DABs was carried out according to the method described in Example 1 with the following modification. After transferring the biotin-labeled agarose particles into the aqueous phase and eliminating unsuitable particle sizes in the exemplary embodiment, the particles are collected in 1×PCR buffer. The concentration of the particles is adjusted to about 4.000/μl. The particles are aliquoted in units of 25 μl.

Forming of the Immune Complex and its Capture:
Reaction Mix:

| | |
|---|---|
| human plasma | 80 μl |
| TBS(K) pH 8.4 (20 mM Tris, 50 mM KCl pH 8.4), 0.5% TritonX-100, 10 mg/ml BS | 10 μl |
| HBR-Plus (Scantibodies) | 10 μl |
| DNA labelled detection antibody | x μl |
| Streptavidin labelled capture antibody | y μl |

Optimization of Antibody Concentration:

Optimal concentration of detection and capture antibodies is determined by conventional immuno-PCR. The concentrations of the two antibodies were systematically varied and immuno-complexes using Troponin-free plasma (negative controls) and troponin-free plasma with defined amounts of spiked Troponin I generated. These were captured on particles, washed and subjected to conventional PCR. Optimum concentration of the respective antibodies is indicated by the lowest limit of detection and broadest dynamic measurement range.

Generating and Capturing the Immune-Complex:

25 μl of reaction mixture (see above) is prepared with the previously determined optimum concentrations of the two antibodies. The reaction mixture is incubated for 10 min at 37° C. at 800 rpm on an Eppendorf thermomixer. The mixture is subsequently mixed with an aliquot of DAB particles (100,000 particles in 25 μl 1× Taq polymerase buffer).

The mixture is incubated on a thermomixer for 5 min at 25° C. at 800 rpm. During this time the binding of the streptavidin-labeled capture antibodies including the immune complexes to the DABs is accomplished. The liquid is applied to a filter with SEFAR PETEX® tissue (w=44 μm) and centrifuged at 300×g. 5 washing steps are performed with 500 μl of TBS (K) pH 8.4 (20 mM Tris, 50 mM KCl pH 8.4), 0.05% TritonX-100, 1 mg/ml BSA. Subsequently tow additional washing steps with 1×Taq DNA polymerase PCR buffer [20 mM Tris HCl (pH 8.4), 50 mM KCl] are performed.

A PCR reaction mixture (volume 25 μl) having the following composition is prepared:

```
                                             (SEQ ID NO: 5)
    500 nM fw-Primer (5' AGCTCTTGATCCGGCAAACA 3')
```

```
                                             (SEQ ID NO: 6)
    500 nM rev-     (5' GCGTCAGACCCCGTAGAAAA 3')
    Primer SYBR ® Green I nucleic acid gel stain (Sigma-
    Aldrich, #S9430) 1:25000

12.5 μl 2x PCR-Mastermix

PCR grade Water
```

DABs are recovered from the sieve by placing the filter in the opposite orientation into the tube. The PCR reaction mix is applied to the filter. Subsequently the unit is centrifuged for 1 min at 1000×g. The DABs are collected at the bottom of centrifuge tube and then incubated for 10 min in the PCR reaction mixture at 25° C. at 800 rpm on a thermomixer.

Performing the PCR Reaction

DABs are transferred to the oil phase as described in embodiment 2. PCR amplification is performed over 40 cycles with the following parameters:

Cycle 1:
5 min 95° C.
30 sec 65° C.
30 sec 72° C.

Cycle 2-40:
30 sec 94° C.
30 sec 65° C.
30 sec 72° C.

After completing amplification the SYBR green signal of the individual particles is detected by means of fluorescence microscopy. Data analysis is performed according to established algorithms for digital PCR.

Determining the Optimal Dynamic Measurement Range

Nonspecific binding of DNA-labeled detection antibody to DABs represents a critical parameter that limits the applicability of digital immuno-PCR. Nonspecifically bound label results in false-positive DABs after amplification. Therefore, in digital immuno-PCR the quantification of the analyte is achieved by determining the difference between a positive sample and a negative control.

In one extreme scenario nonspecific binding of the detection antibody can lead to a majority of DABs with a false-positive signal in control reactions without analytes. This is mitigated by reducing the effective concentration of the detection antibody, either by gradually reducing the concentration of the detection antibody in the assay or maintaining the antibody concentration by increasing dilution of the DNA-labeled detection antibody with the same antibody without DNA label.

Further modifications of the preferred embodiments are possible without leaving the scope of the invention, which is solely defined by the claims./

The features of the present invention disclosed in the specification, the claims, and/or in the accompanying drawings may, both separately and in any combination thereof, be material for realizing the invention in various forms thereof.

The invention claimed is:

1. A method of performing a detection of an analyte in a sample, said method comprising the steps:
   a) providing prefabricated microparticles, each of which has a surface and includes a void volume for receiving an aqueous solution, wherein each of said prefabricated microparticles is dispersible in a non-aqueous medium and, upon dispersion in a non-aqueous medium, provides for a defined reaction space in such non-aqueous medium, in which defined reaction space a chemical or biochemical reaction indicating the presence of an analyte can be performed, and wherein each of said prefabricated microparticles comprises a capture agent that, upon exposure of said prefabricated microparticle to a sample surrounding said prefabricated microparticle and containing an analyte, selectively and specifically binds the analyte to be detected and that, upon binding of the analyte to the capture agent, forms a complex between said capture agent and said analyte, wherein said capture agent binds the analyte from a sample surrounding said prefabricated microparticles, and wherein each of said prefabricated microparticles further comprises a detection agent that is specific for the analyte or said complex between said capture agent and said analyte, and that binds said analyte or said complex between said capture agent and said analyte;

b) exposing said prefabricated microparticles to an aqueous sample suspected of containing an analyte to be detected, thus allowing the capture agent to selectively and specifically bind the analyte to be detected, if present;

c) placing the prefabricated microparticles into a non-aqueous phase, and using the void volume of each of said prefabricated microparticles as a defined reaction space in which a chemical or biochemical reaction indicating the presence of an analyte, is performed, by either d1) detecting the detection agent bound to said analyte or to said complex between said capture agent and said analyte;

or d2) amplifying the analyte, if present, by way of an amplification reaction, and detecting the thus amplified product by means of said detection agent, wherein said analyte is a nucleic acid and said amplification reaction is a nucleic acid amplification, or d3) performing a signal amplification reaction and detecting the thus amplified signal, wherein said reaction space in which said chemical or biochemical reaction indicating the presence of an analyte, is performed, is defined by said void volume of each of said prefabricated microparticles and is not larger than said void volume of each of said prefabricated microparticles.

2. The method according to claim 1, wherein said prefabricated microparticles are provided as prefabricated microparticles which are dried.

3. The method according to claim 2, wherein each of said prefabricated microparticles is reconstituted in an aqueous solution either during step a) or step b), and, upon reconstitution, receives such aqueous solution in its void volume.

4. The method according to claim 1, wherein said prefabricated microparticles are not microparticles that are in-situ generated at the site or in the reaction, at or during which analyte detection is to take place.

5. The method according to claim 1, wherein the capture agent is predominantly located on the surface of each of said prefabricated microparticles, such that the prefabricated microparticles is are capable of enriching and concentrating an analyte located outside of the microparticles.

6. The method according to claim 1, wherein said detection agent is included in said prefabricated microparticles during a prefabrication process or is included in an aqueous solution resulting from reconstitution of the microparticles either during step a) or step b), and thus becomes part of the prefabricated microparticles upon reconstitution.

7. The method according to claim 1, wherein each of said prefabricated microparticles is made of a gel-forming agent, such gel-forming agent being liquefiable upon the application of heat or light, or upon a change of pH, redox potential, ionic strength, temperature, magnetic field or electromagnetic radiation, or upon exposure to an enzyme or, if the gel-forming agent itself comprises an enzyme, to a substrate of such enzyme.

8. The method according to claim 7, wherein said gel-forming agent forms a matrix defining the surface and the void volume of each of said microparticles.

9. The method according to claim 7, wherein said gel-forming agent is selected from
a) synthetic polymers prepared from their corresponding monomers;
b) silicone-based polymers; and
c) naturally occurring polymers selected from polysaccharides, polypeptides, and polynucleotides.

10. The method according to claim 7, wherein, during or after step c), the gel-forming agent is liquefied through the application of heat or light, or by a change of pH, redox potential, ionic strength, temperature, magnetic field or electromagnetic radiation, or upon exposure to an enzyme or, if the gel-forming agent itself comprises an enzyme, to a substrate of such enzyme, resulting in an aqueous droplet in a non-aqueous phase.

11. The method according to claim 1, wherein said capture agent is selected from antibodies or antibody fragments, nucleic acids, Spiegelmers, and non-antibody proteins capable of specifically binding an analyte or analyte complex.

12. The method according to claim 1, wherein said detection agent is selected from antibodies or antibody fragments, nucleic acids, Spiegelmers, and non-antibody proteins, each of them optionally being labelled with a suitable reporter molecule that produces an optically or otherwise detectable signal indicating the presence of the analyte to be detected.

13. The method according to claim 1, wherein each of said prefabricated microparticles is specifically labelled.

14. The method according to claim 1, which is performed using a collection of prefabricated microparticles.

15. The method according to claim 14, wherein, in said collection of prefabricated microparticles, said prefabricated microparticles are different from each other in that they are specific for different analytes to be detected, wherein each prefabricated microparticle is specifically labelled such that different prefabricated microparticles and their corresponding detected analytes can be distinguished by the specific labels of the prefabricated microparticles.

16. The method according to claim 14, wherein the collection of prefabricated microparticles is suspended in the non-aqueous phase and/or is located on a solid substrate isolating each prefabricated microparticle from other prefabricated microparticles, if present, wherein said solid substrate is a filter, a sieve, a substrate having a pattern of wells, recesses, grooves, channels, trenches, craters, holes, or pillars.

17. The method according to claim 1, wherein said method involves the use of prefabricated microparticles or of a collection of prefabricated microparticles, for performing a digital detection of an analyte or a plurality of analytes in a sample or for enriching and concentrating a plurality of analytes in a plurality of defined volumes, wherein all of said defined volumes in said plurality of defined volumes are equal.

18. The method according to claim 1, wherein, after the step of exposing b), there is one or several washing steps.

19. The method according to claim 1, wherein in step a), said prefabricated microparticles are provided in dried form, and, in step b), said prefabricated microparticles are reconstituted in aqueous solution and then exposed to a sample suspected of containing an analyte to be detected, wherein, optionally after the step of reconstituting, there is one or several washing steps.

20. The method according to claim 1, wherein, in step b) a number of prefabricated microparticles and a number of analyte molecules in the sample are maintained or adjusted, as necessary, such that the binding of a single analyte molecule per prefabricated microparticle follows a Poisson distribution such that, on average, there is no more than one analyte molecule bound per microparticle, thus allowing the detection of a single analyte molecule per prefabricated microparticle.

21. The method according to claim 1, wherein, during step c), the prefabricated microparticles are suspended in the non-aqueous phase and/or are located on a solid substrate isolating each prefabricated microparticle from other prefabricated microparticles, if present, wherein said solid substrate is a filter, a sieve, a substrate having a pattern of wells, recesses, grooves, channels, trenches, craters, holes, or pillars.

22. The method according to claim 1, wherein the non-aqueous phase is an oil phase.

* * * * *

UNITED STATES PATENT AND TRADEMARK OFFICE
CERTIFICATE OF CORRECTION

PATENT NO. : 11,073,518 B2  
APPLICATION NO. : 16/475109  
DATED : July 27, 2021  
INVENTOR(S) : Katrin Steinmetzer et al.

Page 1 of 1

It is certified that error appears in the above-identified patent and that said Letters Patent is hereby corrected as shown below:

In the Specification

Column 4:  
Line 27, "in dried faun," should read --in dried form,--.

Column 5:  
Line 39, "such a dye" should read --such as a dye.--.

Column 8:  
Line 33, "each micro particle" should read --each microparticle."--.

Column 15:  
Line 47, "such twin" should read --such term--.

Column 18:  
Line 26, "65 µl." should read --65 pl.--.  
Line 61, "such no accessible" should read --such that no accessible.--.

Column 22:  
Line 51, "the claims./" should read --the claims.--.

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*